United States Patent
Lewis et al.

(10) Patent No.: US 11,535,648 B2
(45) Date of Patent: Dec. 27, 2022

(54) ISOLATED DAROBACTIN A ANALOG COMPOUNDS AND COMPOSITIONS THEREOF

(71) Applicant: Northeastern University, Boston, MA (US)

(72) Inventors: Kim Lewis, Newton, MA (US); Yu Imai, Kobe (JP); Quentin Favre-Godal, Geneva (CH); Akira Iinishi, Newton, MA (US); Kirsten Meyer, Toronto (CA)

(73) Assignee: Northeastern University, Boston, MA (US)

( * ) Notice: Subject to any disclaimer, the term of this patent is extended or adjusted under 35 U.S.C. 154(b) by 0 days.

(21) Appl. No.: 17/260,934

(22) PCT Filed: May 17, 2019

(86) PCT No.: PCT/US2019/032806
§ 371 (c)(1),
(2) Date: Jan. 15, 2021

(87) PCT Pub. No.: WO2020/018173
PCT Pub. Date: Jan. 23, 2020

(65) Prior Publication Data
US 2021/0261616 A1    Aug. 26, 2021

Related U.S. Application Data

(60) Provisional application No. 62/789,313, filed on Jan. 7, 2019, provisional application No. 62/700,746, filed on Jul. 19, 2018.

(51) Int. Cl.
*C07K 7/06* (2006.01)
*A61P 31/04* (2006.01)
*A61K 45/06* (2006.01)

(52) U.S. Cl.
CPC ............... *C07K 7/06* (2013.01); *A61K 45/06* (2013.01); *A61P 31/04* (2018.01)

(58) Field of Classification Search
CPC ................................. A61P 31/04; A61K 45/06
See application file for complete search history.

(56) References Cited

U.S. PATENT DOCUMENTS

| 8,680,087 B2 | 3/2014 | Yang et al. |
| 2014/0031275 A1 | 1/2014 | Lewis et al. |

FOREIGN PATENT DOCUMENTS

| WO | 95/03695 A1 | 2/1995 |
| WO | 2017/176347 A2 | 10/2017 |

OTHER PUBLICATIONS

Tailliez, Phylogeny of Photorhabdus and Xenorhabdus based on universally conserved protein-coding sequences and implications for the taxonomy of these two genera, International Journal of Systematic and Evolutionary Microbiology; 60; 1921-1937 (Year: 2010).*

(Continued)

*Primary Examiner* — Kevin S Orwig
*Assistant Examiner* — John Michael Cronin
(74) *Attorney, Agent, or Firm* — Morgan, Lewis & Bockius LLP

(57) ABSTRACT

Embodiments of the present invention relate to a novel compound of Formula (I) or stereoisomer, a tautomer, or a pharmaceutically acceptable salt thereof, for use in treatment of infection caused by Gram-negative bacteria.

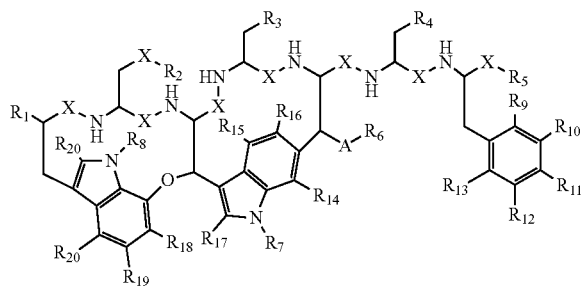

7 Claims, 6 Drawing Sheets

Specification includes a Sequence Listing.

(56) References Cited

OTHER PUBLICATIONS

Hurst, Elucidation of the Photorhabdus temperata Genome and Generation of a Transposon Mutant Library to Identify Motility Mutants Altered in Pathogenesis, Journal of Bacteriology, 197; 13; 2201-2216 (Year: 2015).*
International Search Report issued in corresponding International Patent Application No. PCT/US2019/032806 dated Sep. 5, 2019.
Written Opinion issued in corresponding International Patent Application No. PCT/US2019/032806 dated Sep. 5, 2019.
Extended European Search Report issued in corresponding European Patent Application No. 19837862.2 dated May 9, 2022.
King et al., "Unveiling the Biosynthetic Pathway of the Ribosomally Synthesized and Post-traslationally Modified Peptide Ustiloxin B in Filamentous Fungi," Angewandte Chemie international Edition, vol. 55, No. 28, 8072-8075 (2016).
Hudson et al., "Ripp antibiotics: biosynthesis and engineer potential," Current Opinion in Microbiology, vol. 45, 61-69 (2018).
Bohringer et al,. "Mutasynthetic Production and Antimicrobial Characterization of Darobactin Analogs," Microbiology Spetrum, vol. 9, No. 3 (2021).

* cited by examiner

RP-HPLC chromatogram monitoring at 254 nm for Formula (II) with retention time 12.25 min

FIGURE 6

Efficacy of Formula (II) in a mouse gastrointestinal infection of Salmonella Typhimurium.

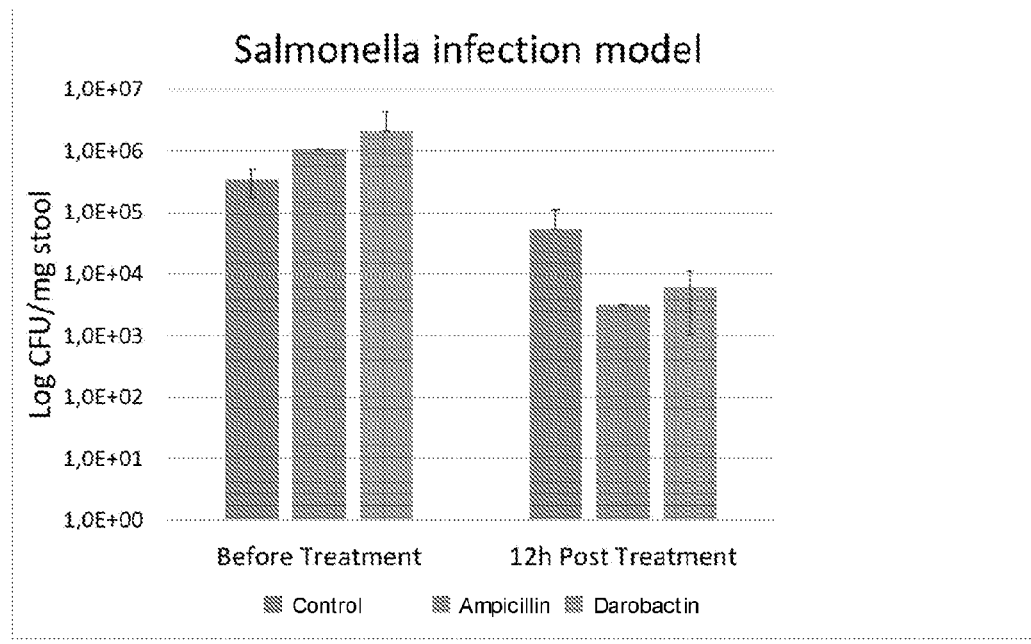

Day 1: C57BL/6 mice (n=3) were treated with 20mg/Kg oral Streptomycin.
Day 2: mice were orally infected with $2 \times 10^8$ *Salmonella* Typhimurium cells.
Day 4: mice received one dose of oral Ampicillin (100mg/Kg) or darobactin (50mg/Kg). Stool samples were collected before and 12h after treatment for *Salmonella* enumeration on selective media.

ISOLATED DAROBACTIN A ANALOG COMPOUNDS AND COMPOSITIONS THEREOF

CROSS-REFERENCE TO RELATED APPLICATION(S)

This application claims the benefit of and priority to U.S. Provisional Application No. 62/700,746, filed on Jul. 19, 2018, and 62/789,313, filed on Jan. 7, 2019, which are incorporated herein by reference in their entireties.

FIELD OF THE INVENTION

The present disclosure relates to a novel antimicrobial compound and its analogues, pharmaceutical compositions comprising said compounds and the use of said compounds and pharmaceutical compositions for treatment. This invention was made with government support under Grant No. P01-AI118687 awarded by the National Institutes of Health. The government has certain rights in the invention.

SEQUENCE LISTING SUBMISSION VIA EFS-WEB

A computer readable text file, entitled "SequenceListing.txt," created on or about Jan. 15, 2021 with a file size of about 2 kb contains the sequence listing for this application and is hereby incorporated by reference in its entirety.

BACKGROUND OF THE INVENTION

In susceptible individuals, certain Gram-negative bacteria can cause serious complications and infections, such as pneumonia, urinary tract infections, wound infections, ear infections, eye infections, intra-abdominal infections, oral bacterial overgrowth and sepsis. The treatment of serious bacterial infections in clinical practice can be complicated by antibiotic resistance. Recent years have seen a rise in infections by Gram-negative bacteria that are resistant to many types of antimicrobials, including broad-spectrum antibiotics such as aminoglycosides, cephalosporins and even carbapenems. This alarming trend highlights the need to identify new antimicrobials that are effective against Gram-negative bacteria, in particular against multidrug-resistant Gram-negative bacteria.

Polymyxins are a class of antibiotics produced by the Gram-positive bacterium *Bacillus polymyxa*. First identified in the late 1940s, polymyxins, particularly polymyxin B and polymyxin E (colistin), were once used in the treatment of Gram-negative infections. However, these antibiotics exhibited side effects such as nephrotoxicity. Consequently, their use in therapy has been limited to treatments of last resort.

SUMMARY OF THE INVENTION

The present invention pertains to a novel compound and its analogues, which exhibit excellent antimicrobial activity—particularly against Gram-negative pathogens. Pharmaceutical compositions containing the novel compound and its analogues are useful for the treatment of prevention of various infectious disease including skin and skin structure infections, respiratory infections, septicemia, bacteremia, and inflammatory bowel diseases (IBD). Embodiments of the invention also relate to treating or preventing a bacterial infection.

In one aspect, the present invention comprises, consists essentially of or consists of a novel compound represented by the following Formula (II):

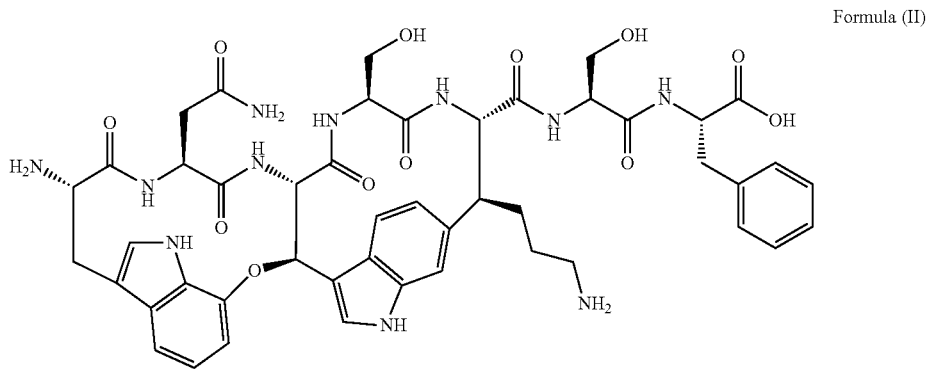 [SMILES: NCCC[C@H]1c2ccc3c(c[nH]c3c2)[C@H]2Oc3cccc4c(c[nH]c34)C[C@H](N)C(=O)N[C@@H](CC(N)=O)C(=O)N[C@@H]2C(=O)N[C@@H](CO)C(=O)N[C@@H]1C(=O)N[C@@H](CO)C(=O)N[C@@H](Cc1ccccc1)C(=O)O]

Formula (II)

and/or pharmaceutically acceptable salts, stereoisomers (including enantiomers), tautomers, or hydrates thereof, as well as analogues Formula (II) (hereinafter, collectively, "Formula (II) compounds"). The present invention also includes pharmaceutical compositions comprising or consisting essentially of Formula (II) compounds, the use of Formula (II) compounds, and method for treating or preventing a bacterial infection with one or more of the Formula (II) compounds.

In another aspect, the present invention comprises, consists essentially of or consists of a novel compound represented by the following Formula (I):

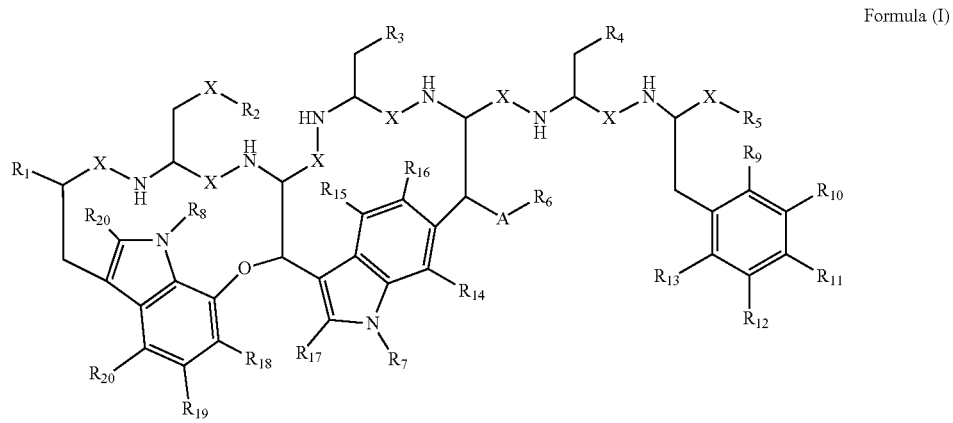

Formula (I)

wherein:

$R_1$, $R_2$, $R_3$, $R_4$, $R_5$, and $R_6$ are each independently selected from the group consisting of hydrogen, alkyl, alkenyl, alkynyl, hydroxyl, hydroxyalkyl, halogen, —CN, —O-alkyl, —C(O)-alkyl, —C(O)O-alkyl, —C(O)OH, —C(O)NH$_2$, —C(O)NH-alkyl, —NH$_2$, —NO$_2$, —CF$_3$, —NH-alkyl, —N-(alkyl)$_2$, —NHC(O)-alkyl and aryl, wherein said alkyl, alkenyl, alkynyl and aryl are each optionally substituted, $R_7$ and $R_8$ are each independently selected from the group consisting of hydrogen, straight or branched C1-C5 alkyl, straight or branched C2-C6 alkenyl, straight or branched C2-C6 alkynyl; wherein said alkyl, alkenyl and alkynyl are each optionally substituted;

$R_9$, $R_{10}$, $R_{11}$, $R_{12}$, $R_{13}$, $R_{14}$, $R_{15}$, $R_{16}$, $R_{17}$, $R_{18}$, $R_{19}$ and $R_{20}$ are each independently selected from the group consisting of hydrogen, alkyl, alkenyl, alkynyl, cycloalkyl, cycloalkenyl, heterocycloalkyl, heterocycloalkenyl, aryl, heteroaryl, haloalkyl, hydroxyl, hydroxyalkyl, halogen, —CN, —O-alkyl, —C(O)-alkyl, —C(O)O-alkyl, —C(O)OH, —C(O)NH$_2$, —C(O)NH-alkyl, —NH$_2$, —NO$_2$, —CF$_3$, —NH-alkyl, —NHC(O)-alkyl, wherein said alkyl, alkenyl, alkynyl, cycloalkyl cycloalkenyl, heterocycloalkyl, heterocycloalkenyl, aryl, heteroaryl, haloalkyl are each optionally substituted;

A is a bond or —(CH$_2$)$_n$—, wherein n is an integer between 0 and 10;

X is —C(O)—, —CH$_2$—, —C(OH)—, —C(O)O-alkyl, —C((O)alkyl)- and/or pharmaceutically acceptable salts, stereoisomers (including enantiomers), tautomers, or hydrates thereof, as well as analogues Formula (I) (hereinafter, collectively, "Formula (I) compounds"). The present invention also includes pharmaceutical compositions comprising or consisting essentially of Formula (I) compounds, the use of Formula (I) compounds, and method for treating or preventing a bacterial infection with one or more of the Formula (I) compounds.

Formula (I) compounds, prodrugs, pharmaceutically acceptable salts, enantiomers, stereoisomers, rotamers, tautomers, diastreomers, and racemates thereof exhibit advantageous antibacterial activity against various Gram-negative bacteria, and is useful for the treatment or prevention of various infectious diseases induced by various bacteria in human and other animals.

The compound of Formula (I) includes the following Formula (Ia):

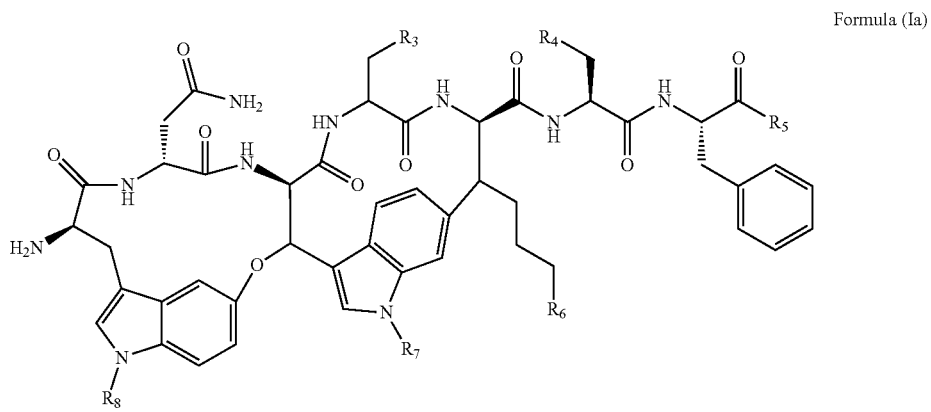

Formula (Ia)

wherein:

R$_3$, R$_4$, R$_5$, R$_6$, R$_7$ and R$_8$ are as defined in the above. and/or pharmaceutically acceptable salts, stereoisomers (including enantiomers), tautomers, or hydrates thereof, as well as analogues Formula (Ia) (hereinafter, collectively, "Formula (Ia) compounds"). The present invention also includes pharmaceutical compositions comprising or consisting essentially of Formula (Ia) compounds, the use of Formula (Ia) compounds, and method for treating or preventing a bacterial infection with one or more of the Formula (Ia) compounds.

Another aspect of the invention relates to a pharmaceutical composition for treating infections in an animal caused by Gram-negative bacteria. In various embodiments, the pharmaceutical composition comprises a therapeutically effective amount of one or more the Formula (I), (Ia) or (II) compounds, or a pharmaceutically acceptable salt thereof, and one or more additional components selected from the group consisting of pharmaceutically acceptable carriers, surfactants, solid diluents, and liquid diluents. The Formula (I), (Ia) or (II) compounds may optionally be present in the form of a pharmaceutically acceptable solvate such as a hydrate.

In general, as used herein, the term "substantially" means±10%, and in some embodiments, ±5% In addition, reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, structures, routines, steps, or characteristics may be combined in any suitable manner in one or more examples of the technology. The headings provided herein are for convenience only and are not intended to limit or interpret the scope or meaning of the claimed technology.

BRIEF DESCRIPTION OF THE DRAWINGS

FIG. 6 is a graph showing the results of in vivo efficacy of the compound of Formula (II) in a mouse gastrointestinal infection of *Salmonella Typhimurium*.

DETAILED DESCRIPTION

Figure 1:
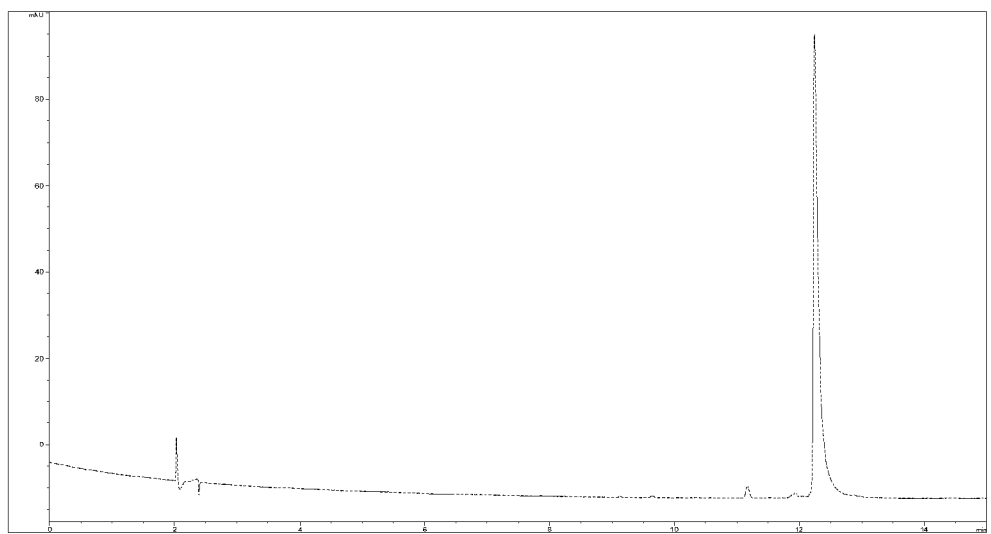
FIG. 1 depicts a reversed-phase high-performance liquid chromatography (RP-HPLC) chromatogram monitoring at 254 nm for the compound of Formula (II) with retention time 12.25 min.
Figure 2:
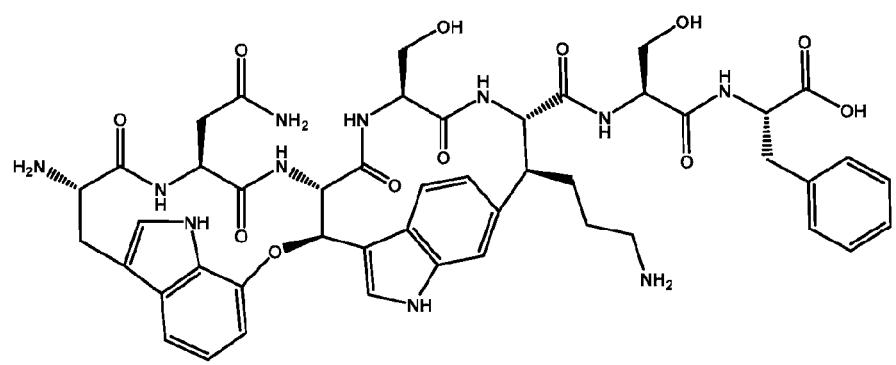
FIG. 2 depicts the chemical structure of a compound according to Formula (II).

As used herein and unless otherwise indicated, the term "compounds of the invention" means, collectively, the compounds of Formulae (I), (Ia) and (II) and pharmaceutically acceptable salts thereof as well as specific compounds depicted herein. The compounds of the invention are identified herein by their chemical structure and/or chemical name. Where a compound is referred to by both a chemical structure and a chemical name, and that chemical structure and chemical name conflict, the chemical structure is determinative of the compound's identity. The compounds of the invention may contain one or more chiral centers and/or double bonds and, therefore, exist as stereoisomers, such as double-bond isomers (i.e., geometric isomers), enantiomers, or diastereomers. According to the invention, the chemical structures depicted herein, and therefore the compounds of the invention, encompass all of the corresponding compound's enantiomers and stereoisomers, that is, both the stereomerically pure form (e.g., geometrically pure, enantiomerically pure, or diastereomerically pure) and enantiomeric and stereoisomeric mixtures. Enantiomeric and stereoisomeric mixtures can be resolved into their component enantiomers or stereoisomers by well-known methods, such as chiral-phase gas chromatography, chiral-phase high performance liquid chromatography, crystallizing the compound as a chiral salt complex, or crystallizing the compound in a chiral solvent. Enantiomers and stereoisomers can also be obtained from stereomerically- or enantiomerically-pure intermediates, reagents, and catalysts by well-known asymmetric synthetic methods. The compounds of the invention are effective against important Gram-negative pathogens. These compounds have good activity against *Escherichia coli, Pseudomonas aeruginosa, Klebsiella pneumoniae, Salmonella Typhimurium* and *Shigella sonnei*. Moreover, the compounds of the invention lack activity against Gram-positive pathogens and are inactive against Gram-negative intestinal symbionts, *Bacteroides*. As detailed below, this selectivity is pharmacologically beneficial. Based on its unusual structure including a C—C link between tryptophan and lysine, compounds of the invention belong to a novel class of antimicrobial agents. Indeed, the last new class of compounds acting against Gram-negative bacteria was discovered 50 years ago.

Selective activity against Gram-negative pathogens is highly unusual, and in fact, there is only one known compound with such properties—polymyxin, which acts by binding to the bacterial lipopolysaccharides (LPS). Compounds in accordance herewith do not bind to LPS and, importantly, are active against polymyxin-resistant mutants. Polymyxin is the antibiotic of last resort against multidrug resistant (MDR) Gram-negative bacteria.

The compounds of the invention have very low resistance and no detectable cytotoxicity. They may be used to treat topical and systemic infections of Gram-negative pathogens, such as skin and skin structure infections, respiratory infections, septicemia and bacteremia.

Another important application of the compounds of the invention follows from their selective activity against enterobacterial pathobionts of the large intestine. In patients with inflammatory bowel disease (IBD), a bloom of enterobacteriaceae, in particular that of *E. coli*, fuels a cycle of inflammation. General broad-spectrum antibiotics are of limited help, since they harm the symbiotic microbiota. The compounds of the invention are inactive against Gram-positive bacteria, and are inactive against *Bacteroides*, the main Gram-negative symbionts of the GI tract. The compounds of the invention may be used to eliminate the bloom of enterobacteria in patients with IBD. The prevalence of enterobacteria is also a general feature of a dysbiotic gut, and will be treated with one or more of the compounds of the invention.

As used herein and unless otherwise indicated, the term "alkyl" means a substituted or unsubstituted, saturated, linear or branched hydrocarbon chain radical. Examples of alkyl groups include, but are not limited to, $C_{1-15}$ linear, branched or cyclic alkyl, such as methyl, ethyl, propyl, isopropyl, cyclopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, sec-butyl, t-butyl, cyclobutyl, pentyl, isopentyl, neopentyl, hexyl, and cyclohexyl and longer alkyl groups, such as heptyl, octyl, nonyl and decyl. An alkyl can be unsubstituted or substituted with one or two suitable substituents.

As used herein and unless otherwise indicated, the terms "alkoxy" or "alkyloxy" means an —O-alkyl, wherein alkyl is as defined herein. An alkoxy can be unsubstituted or substituted with one or two suitable substituents. Preferably, the alkyl chain of an alkyloxy is from 1 to 5 carbon atoms in length, referred to herein, for example, as "$C_{1-5}$ alkoxy." In one embodiment, the alkyl chain of an alkyloxy is from 1 to 10 carbon atoms in length, referred to herein, for example, as "$C_{1-10}$ alkoxy."

As used herein and unless otherwise indicated, the terms "alkene" or "alkenyl group" means a monovalent linear, branched or cyclic hydrocarbon chain having one or more double bonds therein. The double bond of an alkene can be unconjugated or conjugated to another unsaturated group. An alkene can be unsubstituted or substituted with one or two suitable substituents. Suitable alkenes include, but are not limited to $C_{2-8}$ alkenyl groups, such as vinyl, allyl, butenyl, pentenyl, hexenyl, butadienyl, pentadienyl, hexadienyl, 2-ethylhexenyl, 2-propyl-2-butenyl, 4-(2-methyl-3-butene)-pentenyl. An alkene can be unsubstituted or substituted with one or two suitable substituents.

As used herein and unless otherwise indicated, the terms "alkynyl" means an unsaturated straight or branched hydrocarbon having at least one carbon-carbon triple bond. Examples of alkynyl groups include, but are not limited to, ethynyl, propynyl, butynyl, pentynyl, hexynyl, methylpropynyl, 4-methyl-1-butynyl, 4-propyl-2-pentynyl, and 4-butyl-2-hexynyl.

As used herein and unless otherwise indicated, the term "aryl" or "aromatic ring" means a monocyclic or polycyclic conjugated ring structure that is well known in the art. Examples of suitable aryl groups or aromatic rings include, but are not limited to, phenyl, tolyl, anthacenyl, fluorenyl, indenyl, azulenyl, and naphthyl. An aryl group can be unsubstituted or substituted with one or two suitable substituents. In one embodiment, the aryl group is a monocyclic ring, wherein the ring comprises 6 carbon atoms, referred to herein as "$C_6$ aryl."

"Substituted aryl" includes an aryl group optionally substituted with one or more functional groups, such as halo, alkyl, haloalkyl (e.g., trifluoromethyl), alkoxy, haloalkoxy (e.g., difluoromethoxy), alkenyl, alkynyl, aryl, heteroaryl, arylalkyl, aryloxy, aryloxyalkyl, arylalkoxy, alkoxycarbonyl, alkylcarbonyl, arylcarbonyl, arylalkenyl, aminocarbonylaryl, arylthio, arylsulfinyl, arylazo, heteroarylalkyl, heteroarylalkenyl, heteroaryloxy, hydroxy, nitro, cyano, amino, substituted amino wherein the amino includes 1 or 2 substituents (which are optionally substituted alkyl, aryl or any of the other substituents recited herein), thiol, alkylthio, arylthio, heteroarylthio, arylthioalkyl, alkoxyarylthio, alkylaminocarbonyl, arylaminocarbonyl, aminocarbonyl, alkylcarbonyloxy, arylcarbonyloxy, alkylcarbonylamino, arylcarbonylamino, arylsulfinyl, arylsulfinylalkyl, arylsulfonylamino, or arylsulfonaminocarbonyl and/or any of the alkyl substituents recited herein.

The term "heteroaryl" as used herein alone or as part of another group refers to a 5- to 7-membered aromatic ring which includes 1, 2, 3 or 4 hetero atoms such as nitrogen, oxygen or sulfur and such rings fused to an aryl, cycloalkyl, heteroaryl or heterocycloalkyl ring (e.g. benzothiophenyl, indolyl), and includes possible N-oxides. "Substituted heteroaryl" includes a heteroaryl group optionally substituted with 1 to 4 substituents, such as the substituents included above in the definition of "substituted alkyl" and "substituted cycloalkyl." Substituted heteroaryl also includes fused heteroaryl groups which include, for example, quinoline, isoquinoline, indole, isoindole, carbazole, acridine, benzimidazole, benzofuran, isobenzofuran, benzothiophene, phenanthroline, purine, and the like.

Moreover, the terms "heterocyclo," "heterocycle," or "heterocyclic ring," as used herein, refer to an unsubstituted or substituted stable 5- to 7-membered monocyclic ring system which may be saturated or unsaturated, and which consists of carbon atoms and from one to four heteroatoms selected from N, O or S, and wherein the nitrogen and sulfur heteroatoms may optionally be oxidized, and the nitrogen heteroatom may optionally be quaternized. The heterocyclic ring may be attached at any heteroatom or carbon atom which results in the creation of a stable structure. Examples of such heterocyclic groups include, but are not limited to, piperidinyl, piperazinyl, oxopiperazinyl, oxopiperidinyl, oxopyrrolidinyl, oxoazepinyl, azepinyl, pyrrolyl, pyrrolidinyl, furanyl, thienyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isooxazolyl, isoxazolidinyl, morpholinyl, thiazolyl, thiazolidinyl, isothiazolyl, thiadiazolyl, tetrahydropyranyl, thiamorpholinyl, thiamorpholinylsulfoxide, thiamorpholinylsulfone, and oxadiazolyl.

As used herein, the term "optionally substituted" may indicate that a chemical moiety referred to, for example, alkyl, aryl, heteroaryl, may be unsubstituted or substituted with one or more groups including, without limitation, alkyl, alkenyl, alkynyl, cycloalkyl, arylalkyl, aryl, heterocycle, heteroaryl, hydroxyl, amino, alkoxy, halogen, carboxy, carbalkoxy, carboxamido, monoalkylaminosulfinyl, dialkylaminosulfinyl, monoalkylaminosulfonyl, dialkylaminosulfonyl, alkylsulfonylamino, hydroxysulfonyloxy, alkoxysulfonyloxy, alkylsulfonyloxy, hydroxysulfonyl, alkoxysulfonyl, alkylsulfonylalkyl, monoalkylaminosulfonylalkyl, dialkylaminosulfonylalkyl, monoalkylaminosulfinylalkyl, dialkylaminosulfinylalkyl and the like. The chemical moieties of Formula I may be optionally substituted alkyl, alkenyl, alkynyl, cycloalkyl, arylalkyl, aryl, heterocycle or heteroaryl. For example, optionally substituted alkyl may include both propyl and 2-chloro-propyl. Additionally, "optionally substituted" is also inclusive of embodiments where the named substituent or substituents have multiple substituents rather than simply a single substituent. For example, optionally substituted aryl may include both phenyl and 3-methyl-5-ethyl-6-chloro-phenyl.

The term "cycloalkyl" includes saturated or partially unsaturated (containing 1 or more double bonds) cyclic hydrocarbon groups containing 1 to 3 rings, including monocyclicalkyl, bicyclicalkyl and tricyclicalkyl, containing a total of 3 to 20 carbons forming the rings, or about 3 to 10 carbons, forming the ring and which may be fused to 1 or 2 aromatic rings as described for aryl, which include cyclopropyl, cyclobutyl, cyclopentyl, cyclohexyl, cycloheptyl, cyclooctyl, cyclodecyl, cyclododecyl, and cyclohexenyl.

"Substituted cycloalkyl" includes a cycloalkyl group optionally substituted with 1 or more substituents such as halogen, alkyl, substituted alkyl, alkoxy, hydroxy, aryl, substituted aryl, aryloxy, cycloalkyl, alkylamido, alkanoylamino, oxo, acyl, arylcarbonylamino, amino, nitro, cyano, thiol and/or alkylthio and/or any of the substituents included in the definition of "substituted alkyl."

The term "cycloalkenyl" includes a nonaromatic monocyclic or bicyclic carbocyclic ring containing at least one double bond. Examples of cycloalkenyl groups include, but are not limited to, cyclopropenyl, cyclobutenyl, cyclopentenyl, cyclohexenyl, cycloheptenyl, cyclooxtenyl and the like.

As used herein and unless otherwise indicated, the term "aryloxy" means an —O-aryl group, wherein aryl is as defined herein. An aryloxy group can be unsubstituted or substituted with one or two suitable substituents. Preferably, the aryl ring of an aryloxy group is a monocyclic ring, wherein the ring comprises 6 carbon atoms, referred to herein as "$C_6$ aryloxy."

As used herein and unless otherwise indicated, the term "ether" means a group of formula alkyl-O-alkyl, alkyl-O-alkynyl, alkyl-O-aryl, alkenyl-O-alkenyl, alkenyl-O-alkynyl, alkenyl-O-aryl, alkynyl-O-alkynyl, alkynyl-O-aryl, aryl-O-aryl, wherein "alkyl", "alkenyl", "alkynyl" and "aryl" are defined herein.

As used herein and unless otherwise indicated, the term "carboxy" means a radical of the formula: —COOH.

As used herein and unless otherwise indicated, the term "halogen" means fluorine, chlorine, bromine, or iodine. Correspondingly, the meaning of the terms "halo" and "Hal" encompass fluoro, chloro, bromo, and iodo.

As used herein and unless otherwise indicated, the terms "substituted" and "suitable substituent" mean groups that do not nullify the synthetic or pharmaceutical utility of the compounds of the invention or the intermediates useful for preparing them. Examples of substituted groups or suitable substituents include, but are not limited to: $C_{1-10}$ alkyl; $C_{1-10}$ alkenyl; $C_{1-10}$ alkynyl; $C_6$ aryl; $C_{3-5}$ heteroaryl; $C_{3-7}$ cycloalkyl; $C_{1-10}$ alkoxy; $C_6$ aryloxy; —CN; —OH; SH; oxo; halo; —$NO_2$; —$CO_2H$; —$NH_2$; —NHOH; —NH($C_{1-10}$ alkyl); —N($C_{1-10}$ alkyl)$_2$; —NH($C_6$ aryl); —NHO($C_{1-10}$ alkyl); —N(O$C_{1-10}$ alkyl)$_2$; —NH(O$C_6$ aryl); —S($C_{1-10}$ alkyl); —S($C_6$ aryl); (=O); —N($C_6$ aryl)$_2$; —CHO; —C(O)($C_{1-10}$ alkyl); —C(O)($C_6$ aryl); —C(O)O($C_{1-10}$ alkyl); and —C(O)O($C_6$ aryl), —C(S)($C_{1-10}$ alkyl); —C(S)($C_6$ aryl); —$SO_2$($C_{1-10}$ alkyl); —$SO_2$($C_6$ aryl), —SO($C_{1-10}$ alkyl); —SO($C_6$ aryl), and —$SO_3H$, —C(S)O($C_{1-10}$ alkyl); —C(S)O$C_6$ aryl. In certain illustrative embodiments, the substituents can be one or more than one suitable groups, such as, but not limited to, —F, —Cl, —Br, —I, —OH, azido, —SH, alkyl, aryl, heteroalky, alkyoxyl, alkylthiol, amino, hydroxylamino, N-alkylamino, —N,N-dialkylamino, —N,N-dimethylamino, acyl, alkyloxycarbonyl, sulfonyl, urea, —$NO_2$, and triazolyl. One of skill in art can readily choose a suitable substituent based on the stability and pharmacological and synthetic activity of the compound of the invention.

The phrase "pharmaceutically acceptable salt(s)," as used herein includes but is not limited to salts of acidic or basic groups that may be present in the compounds (including the compounds of the invention) used in the present compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions including, but not limited to, sulfuric, citric, maleic, acetic, oxalic, hydrochloride, hydrobromide, hydroiodide, nitrate, sulfate, bisulfate, phosphate, acid phosphate, isonicotinate, acetate, lactate, salicylate, citrate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds included in the present compositions that include an amino moiety may form pharmaceutically acceptable salts with various amino acids, in addition to the acids mentioned above. Compounds included in the present compositions that are acidic in nature are capable of forming base salts with various pharmacologically acceptable cations. Examples of such salts include alkali metal or alkaline earth metal salts and, particularly, calcium, magnesium, sodium, lithium, zinc, potassium and iron salts.

As used herein, the term "pharmaceutically acceptable prodrug" means a derivative of a compound that can hydrolyze, oxidize, or otherwise react under biological conditions, in vitro or in vivo, to provide the compound. Examples of prodrugs include, but are not limited to, compounds that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include but are not limited to compounds that comprise oligonucleotides, peptides, lipids, aliphatic and aromatic groups, or NO, NO$_2$, ONO, and ONO$_2$ moieties. Prodrugs can typically be prepared using well known methods.

In one aspect, provided herein are methods of treating, ameliorating, or preventing a bacterial infection in a subject in need thereof, comprising administering to the subject a therapeutically effective amount of at least one of the compounds of Formula (I), Formula (Ia) or Formula (II), or at least one of the specific compounds described herein. Administration of the compound may be topical, such as subcutaneous, transdermal, rectal, intravaginal, intranasal, intrabronchial, intraocular, or intra-aural. Alternatively, administration may be systemic, such as oral administration. In still other alternatives, administration may be parenteral, intravenous, intramuscular, or intraperitoneal.

As used herein, the term "administration" can also include administering a combination of compounds. Thus, administration may be in the form of dosing an organism with a compound or combination of compounds, such that the organism's circulatory system will deliver a compound or combination of compounds to the target area, including but not limited to a cell or cells, synaptic junctions and circulation. Administration may also mean that a compound or combination of compounds is placed in direct contact with an organ, tissue, area, region, cell or group of cells, such as but not limited to direct injection of the combination of compounds.

In select embodiments, a combination of compounds can be administered, and thus the individual compounds can also be said to be co-administered with one another. As used herein, "co-administer" indicates that each of at least two compounds is administered during a time frame wherein the respective periods of biological activity or effects overlap. Thus the term co-administer includes sequential as well as coextensive administration of the individual compounds, at least one of which is a compound of the present invention. Accordingly, "administering" a combination of compounds according to some of the methods of the present invention includes sequential as well as coextensive administration of the individual compounds of the present invention. Likewise, the phrase "combination of compounds" indicates that the individual compounds are co-administered, and the phrase "combination of compounds" does not mean that the compounds must necessarily be administered contemporaneously or coextensively. In addition, the routes of administration of the individual compounds need not be the same.

As used herein, the terms "treat" and "treatment" refer to a slowing of or a reversal of the progress of the disease or infection. Treating a disease includes treating a symptom and/or reducing the symptoms of the disease or infection. The term "preventing" refers to a slowing of the disease or of the onset of the disease, infection or the symptoms thereof. Preventing a disease or infection can include stopping the onset of the disease, infection or symptom thereof.

As used herein, the term "subject" may be an animal, vertebrate animal, mammal, rodent (e.g., a guinea pig, a hamster, a rat, a mouse), a murine (e.g., a mouse), a canine (e.g., a dog), a feline (e.g. a cat), an equine (e.g., a horse), a primate, a simian (e.g., a monkey or ape), a monkey (e.g., marmoset, a baboon), an ape (e.g., gorilla, chimpanzee, orangutan, gibbon), or a human.

As used herein, the term "dosage unit" refers to a physically discrete unit, such as a capsule or tablet suitable as a unitary dosage for a subject. Each unit contains a predetermined quantity of a compound of Formula (I), (Ia) or (II) which was discovered or believed to produce the desired pharmacokinetic profile which yields the desired therapeutic effect. The dosage unit is composed of a compound of Formula (I), (Ia) or (II) in association with at least one pharmaceutically acceptable carrier, salt, excipient or a combination thereof. The term "dose" or "dosage" refers to the amount of active ingredient that an individual takes or is administered at one time.

The term "therapeutically effective amount" refers to the amount sufficient to produce a desired biological effect in a subject. Accordingly, a therapeutically effective amount of a compound may be an amount which is sufficient to treat or prevent a disease or infection, and/or delay the onset or progression of a disease or infection, and or alleviate one or more symptoms of the disease or infection, when administered to a subject suffered from or susceptible to that disease or infection. A "pharmaceutically acceptable carrier" or "pharmaceutically acceptable excipient" herein refers to a non-API (where API refers to Active Pharmaceutical Ingredient) substances such as disintegrators, binders, fillers, and lubricants used in formulating pharmaceutical products. They are generally safe for administering to humans.

The term "pharmaceutically acceptable" means approved by a regulatory agency of the Federal or a state government or listed in the U.S. Pharmacopeia or other generally recognized pharmacopeia for use in animals, and more particularly in humans. The term "vehicle" refers to a diluent, adjuvant, excipient, or carrier with which a compound of the invention is administered. Such pharmaceutical vehicles can be liquids, such as water and oils, including those of petroleum, animal, vegetable or synthetic origin, such as peanut oil, soybean oil, mineral oil, sesame oil and the like. The pharmaceutical vehicles can be saline, gum acacia, gelatin, starch paste, talc, keratin, colloidal silica, urea, and the like. In addition, auxiliary, stabilizing, thickening, lubricating and coloring agents may be used. In one embodiment, when administered to a patient, the combination of compounds of the invention and pharmaceutically acceptable vehicles are sterile. Water and/or oils are one vehicle when the combination of compounds of the invention is administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present combination of compounds, if desired, can also contain minor amounts of wetting or emulsifying agents, or pH buffering agents.

In general, each of the individual compounds of the invention may also be administered by any convenient route, for example, orally, by infusion or bolus injection, or by absorption through epithelial or mucocutaneous linings (e.g., oral mucosa, rectal and intestinal mucosa, etc.), and may be administered together with another biologically active agent. Administration can be systemic or local. Various delivery systems are known, e.g., encapsulation in liposomes, microparticles, microcapsules, capsules, etc., and can be used to administer at least one of the compounds of the invention. Methods of administration of the individual compounds include but are not limited to intradermal, intramuscular, intraperitoneal, intravenous, subcutaneous, intranasal, epidural, oral, sublingual, intranasal, intracerebral, intravaginal, transdermal, rectal, pulmonary or topical, particularly to the ears, nose, eyes, or skin. The preferred mode of administration is left to the discretion of the practitioner, and will depend, in part, upon the site of the medical condition.

In specific embodiments, it may be desirable to administer one or more compounds of the combination locally to the area in need of treatment. This may be achieved, for example, and not by way of limitation, by local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers.

Pulmonary administration can also be employed, e.g., by use of an inhaler or nebulizer, and formulation with an aerosolizing agent, or via perfusion in a fluorocarbon or synthetic pulmonary surfactant. In certain embodiments, the compounds of the invention can be formulated as a suppository, with traditional binders and vehicles such as triglycerides.

In another embodiment, the compounds of the invention can be delivered in a vesicle, in particular a liposome (see Langer, 1990, Science 249:1527-1533; Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327).

In yet another embodiment, at least one of the compounds used in the methods of the invention can be delivered in a controlled-release system. In one embodiment, a pump may be used (see Langer, supra; Sefton, 1987, CRC Crit. Ref. Biomed. Eng. 14:201; Buchwald et al., 1980, Surgery 88:507 Saudek et al., 1989, N. Engl. I. Med. 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 1983, J. Macromol. Sci. Rev. Macromol. Chem. 23:61; see also Levy et al., 1985, Science 228:190; During et al., 1989, Ann. Neurol. 25:351; Howard et al., 1989, J. Neurosurg. 71:105). In yet another embodiment, a controlled-release system can be placed in proximity of an organ, e.g., the liver, thus requiring only a fraction of the systemic dose (see, e.g., Goodson, in Medical Applications of Controlled Release, supra, vol. 2, pp. 115-138 (1984)). Other controlled-release systems discussed in the review by Langer, 1990, Science 249:1527-1533) may be used.

Each of the individual compounds to be administered can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In one embodiment, the pharmaceutically acceptable vehicle is a capsule (see e.g., U.S. Pat. No. 5,698,155). Other examples of suitable pharmaceutical vehicles are described in Remington's Science and Practice of Pharmacy (21st ed., Hendrickson, R., et al., Eds., Lippincott Williams & Wilkins, Baltimore, Md. (2006)), which is incorporated by reference.

Typically, when the individual compounds of the invention are administered intravenously, the compounds are in sterile isotonic aqueous buffered solutions. Where necessary, the individual compounds of the invention may also include a solubilizing agent. The individual compounds of the invention for intravenous administration may optionally include a local anesthetic such as lidocaine to ease pain at the site of the injection.

In one embodiment, individual compounds are supplied either together in a unit dosage form or separately. Regardless, compounds may be supplied, for example, as a dry lyophilized powder or water free concentrate in a hermetically sealed container such as an ampoule indicating the quantity of active agent. Where the compound or combination of compounds of the invention are to be administered by infusion, they can be dispensed, for example, with an infusion bottle containing sterile pharmaceutical grade water or saline. Where the compound or combination of compounds of the invention is administered by injection, an ampoule of sterile water for injection or saline can be provided so that the ingredients may be mixed prior to administration.

Compositions for oral delivery may be in the form of tablets, lozenges, aqueous or oily suspensions, granules, powders, emulsions, capsules, syrups, or elixirs, for example. Orally administered compositions may contain one or more optional agents, for example, sweetening agents such as fructose, aspartame or saccharin; flavoring agents such as peppermint, oil of wintergreen, or cherry; coloring agents; and preserving agents, to provide a pharmaceutically palatable preparation. Immediate release formulations for oral use include tablets or capsules containing the active ingredient(s) in a mixture with non-toxic pharmaceutically acceptable excipients. These excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, mannitol, sorbitol, acacia, alginic acid, sodium alginate, gelatin, starch, pregelatmized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like as are found, for example, in The Handbook of Pharmaceutical Excipients, third edition, edited by Arthur H. Kibbe, American Pharmaceutical Association Washington D.C.

Moreover, where in tablet or pill form, the compositions may be coated to delay disintegration and absorption in the gastrointestinal tract thereby providing a sustained action over an extended period of time. Selectively permeable membranes surrounding an osmotically active driving compound are also suitable for orally administered compounds of the invention. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate may also be used. Oral compositions can include standard vehicles such as mannitol, lactose, starch, magnesium stearate, sodium saccharine, cellulose, magnesium carbonate, etc. Such vehicles are preferably of pharmaceutical grade.

For oral delivery, the active compounds can be incorporated into a formulation that includes pharmaceutically acceptable carriers such as binders (e.g., gelatin, cellulose, gum tragacanth), excipients (e.g., starch, lactose), disintegrating agents (e.g., alginate, Primogel, and corn starch), and sweetening or flavoring agents (e.g., glucose, sucrose, saccharin, methyl salicylate, and peppermint). The formulation can be orally delivered in the form of enclosed gelatin capsules or compressed tablets. The capsules and tablets can also be coated with various coating known in the art to modify the flavors, tastes, colors, and shapes of the capsules and tablets. The carrier may be solid or a liquid, or both, and may be formulated with at least one compound described herein as the active compound which may contain from about 0.05% to about 95% by weight of the at least one active compound. Suitable oral formulations can also be in the form of suspension, syrup, chewing gum, wafer, elixir, and the like.

If desired, conventional agents for modifying flavors, tastes, colors, and shapes of the special forms can also be included. In addition, for convenient administration by enteral feeding tube in patients unable to swallow, the active compounds can be dissolved in an acceptable lipophilic vegetable oil vehicle such as olive oil, corn oil and safflower oil.

The active compounds can also be administered parenterally in the form of solution or suspension, or in lyophilized form capable of conversion into a solution or suspension form before use. In such formulations, diluents or pharmaceutically acceptable carriers such as sterile water and physiological saline buffer can be used. Other conventional solvents, pH buffers, stabilizers, anti-bacteria agents, surfactants, and antioxidants can all be included. For example, useful components include sodium chloride, acetates, citrates or phosphates buffers, glycerin, dextrose, fixed oils, methyl parabens, polyethylene glycol, propylene glycol, sodium bisulfate, benzyl alcohol, ascorbic acid, and the like. The parenteral formulations can be stored in any conventional containers such as vials and ampoules.

Routes of topical administration include nasal, bucal, mucosal, rectal, or vaginal applications. For topical administration, the active compounds can be formulated into lotions, creams, ointments, powders, pastes, sprays, suspensions, drops and aerosols. Thus, one or more thickening agents, humectants, and stabilizing agents can be included in the formulations. Examples of such agents include, but are not limited to, polyethylene glycol, sorbitol, xanthan gum, petrolatum, beeswax, or mineral oil, lanolin, squalene, and the like. A special form of topical administration is delivery by a transdermal patch. Methods for preparing transdermal patches are disclosed, e.g., in Brown, et al. (1988) *Ann. Rev. Med.* 39:221-229 which is incorporated herein by reference. Carriers and excipients which may be used include Vaseline, lanoline, polyethylene glycol, alcohols, and combination of two or more thereof. The active compound is generally present at a concentration of from about 0.1% to about 80% w/w of the composition, for example from about 0.2% to 50%.

Subcutaneous implantation for sustained release of the active compounds may also be a suitable route of administration. This entails surgical procedures for implanting an active compound in any suitable formulation into a subcutaneous space, e.g., beneath the anterior abdominal wall. See, e.g., Wilson et al. (1984) *J. Clin. Psych.* 45:242-247. Hydrogels can be used as a carrier for the sustained release of the active compounds. Hydrogels are generally known in the art. They are typically made by crosslinking high molecular weight biocompatible polymers into a network, which swells in water to form a gel like material. Preferably, hydrogels are biodegradable or biosorbable. For purposes of this invention, hydrogels made of polyethylene glycols, collagen, or poly(glycolic-co-L-lactic acid) may be useful. See, e.g., Phillips et al. (1984) *J. Pharmaceut. Sci.*, 73: 1718-1720.

The amount of each individual compounds to be administered will depend on the nature or severity of the symptoms, and can be determined by standard clinical techniques. In addition, in vitro or in vivo assays may optionally be employed to help identify optimal dosage ranges for each of the components of the combination. The precise dose of each component to be employed will also depend on the route of administration and the seriousness of the disease or disorder, and a practitioner can determine these doses based upon each patient's circumstances. In general, however, suitable dosage ranges for oral administration of each of the Formula (I) compounds, the Formula (Ia) compounds, and the Formula (II) compounds are generally about 0.001 mg to 1000 mg of a compound of the invention per kilogram body weight. In specific embodiments of the invention, the oral dose for each component is 0.01 mg to 100 mg per kilogram body weight, more specifically 0.1 mg to 50 mg per kilogram body weight, more specifically 0.5 mg to 20 mg per kilogram body weight, and yet even more specifically 1 mg to 10 mg per kilogram body weight. In one embodiment, the oral dosage of each of the Formula (I) compounds, the Formula (Ia) compounds, and the Formula (II) compounds is at least about 1, 5, 10, 25, 50, 100, 200, 300, 400, or 500 mg/day up to as much as 600, 700, 800, 900, 1000 mg/day for three to fifteen days. Each of the Formula (I) compounds, the Formula (Ia) compounds, and the Formula (II) compounds may be given daily (e.g., once, twice, three times or four times daily) or less frequently (e.g., once every other day, or once or twice weekly). The dosage amounts described herein refer to individual amounts administered. When more than one compound is administered, the preferred dosages correspond to the total amount of the compounds of the invention administered. The oral compositions described herein may contain from about 10% to about 95% active ingredient by weight.

In general, suitable dosage ranges for intravenous (i.v.) administration of individual components are 0.001 mg to 1000 mg per kilogram body weight, 0.01 mg to 100 mg per kilogram body weight, 0.1 mg to 50 mg per kilogram body weight, and 1 mg to 10 mg per kilogram body weight. In general, suitable dosage ranges for intranasal administration of the individual components are generally from about 0.01 pg/kg body weight to 1 mg/kg body weight. In general, suppositories generally contain between about 0.01 mg to 50 mg of a compound per kilogram body weight and may comprise active ingredient in the range of 0.5% to 10% by weight. Effective doses may be extrapolated from dose-response curves derived from in vitro or animal model test systems. Such animal models and systems are well known in the art.

The invention also pertains to pharmaceutical packs or kits comprising one or more containers filled with one or more compounds to be administered in practicing the methods of the invention. Optionally associated with such container(s) can be a notice in the form prescribed by a governmental agency regulating the manufacture, use or sale of pharmaceuticals or biological products, which notice reflects approval by the agency of manufacture, use or sale for human administration. In a certain embodiment, the kit contains more than one compound.

The compounds described herein are useful in the treatment of infections by bacteria which are susceptible or multidrug resistant, polymyxin resistant mutant, carbapenam-resistant bacteria, methicillin-resistant *Staphylococcus*

*aureus*, vanccomycin-resistant Enterococci or multi-drug resistant *Neisseria gonorrhoeae*.

Examples of Gram-negative bacteria include, but are not limited to, *Escherichia coli, Pseudomonas aeruginosa, Candidatus liberibacter, Agrobacterium tumefaciens, Branhamella catarrhalis, Citrobacter di versus, Enterobacter aerogenes, Klebsiella pneumoniae, Proteus mirabilis, Salmonella typhimurium, Neisseria meningitidis, Serratia marcescens, Shigella sonnei, Shigella boydii, Neisseria gonorrhoeae, Acinetobacter baumannii, Salmonella enteriditis, Fusobacterium nucleatum, Veillonella parvula, Actinobacillus actinomycetemcomitans, Aggregatibacter actinomycetemcomitans, Porphyromonas gingivalis, Helicobacter pylori, Francisella tularensis, Yersinia pestis, Vibrio cholera, Morganella morganii, Edwardsiella tarda, Campylobacter jejuni,* or *Haemophilus influenza, Enterobacter cloacae.* and numerous others. Other notable groups of Gram-negative bacteria include the cyanobacteria, spirochaetes, green sulfur and green non-sulfur bacteria.

Medically relevant Gram-negative cocci include three organisms that cause a sexually transmitted disease (*Neisseria gonorrhoeae*), a meningitis (*Neisseria meningitidis*), and respiratory symptoms (*Moraxella catarrhalis*).

Medically relevant Gram-negative bacilli include a multitude of species. Some of them primarily cause respiratory problems (*Hemophilus influenzae, Klebsiella pneumoniae, Legionella pneumophila, Pseudomonas aeruginosa*), primarily urinary problems (*Escherichia coli, Enterobacter cloacae*), and primarily gastrointestinal problems (*Helicobacter pylori, Salmonella enterica*).

Gram-negative bacteria associated with nosocomial infections include *Acinetobacter baumannii*, which causes bacteremia, secondary meningitis, and ventilator-associated pneumonia in intensive-care units of hospital establishments. In one embodiment the compounds and compositions of the present invention are useful in the treatment of infection of one or more of the following Gram-negative bacteria: *E. coli, S. enterica, Klebsiella: K pneumoniae, K. oxytoca; Enterobacter: E. cloacae, E. aerogenes, E. agglomerans, Acinetobacter: A. calcoaceticus, A. baumannii; Pseudomonas aeruginosa, Stenotrophomonas maltophila, Providencia stuartii, Proteus:, P. mirabilis, P. vulgaris.*

In one embodiment, compounds of Formula (I), (Ia) or (II) or pharmaceutically acceptable salts thereof or compositions comprising the same are useful for the treatment of *Pseudomonas* infections including *P. aeruginosa* infection, for example, skin and soft tissue infections, gastrointestinal infection, urinary tract infection, pneumonia and sepsis.

In one embodiment, compounds of Formula (I), (Ia) or (II), or pharmaceutically acceptable salts thereof, or compositions comprising the same are useful for the treatment of *Acinetobacter* infections including *A. baumanii* infection, for pneumonia, urinary tract infection and sepsis.

In one embodiment, compounds of Formula (I), (Ia) or (II), or pharmaceutically acceptable salts thereof, or compositions comprising the same are useful for the treatment of *Klebsiella* infections including *K. pneumoniae* infection, for pneumonia, urinary tract infection, meningitis and sepsis.

In one embodiment, compounds of Formula (I), (Ia) or (II), or pharmaceutically acceptable salts thereof, or compositions comprising the same are useful for the treatment of *E. coli* infection including *E. coli* infections, for bacteremia, cholecystitis, cholangitis, urinary tract infection, neonatal meningitis and *pneumoniae*.

The compounds of the invention may be prepared by growing, under controlled conditions, a strain of microorganism, *Photorhabdus khanii* DSM 3369. The compound is obtained by fermentation and recovered in substantially pure form as described herein. In particular, the instant compound may be produced by a strain of *Photorhabdus P. khanii* DSM 3369 during the aerobic fermentation of suitable nutrient media under the conditions described hereinafter. The media such as those used for the production of many antimicrobial substances are suitable for use in this process for the production of the present compound.

One embodiment of the invention comprises a process suitable for producing antibiotic agents, for example, Formula (II), by submerged aerobic fermentation of *Photorhabdus khanii* DSM 3369. The compound of Formula (II) may be recovered from the fermentation broth by resin absorption and eluted from the resin by washing with solvents of various polarities. Purification may be furthered by chromatographic separation such as reverse-phase high-performance chromatography (RP-HPLC).

Additional microorganisms capable of producing one or more compounds of the present invention include mutant species, which show advantageous properties compared with species known in the art. Such bacterial strains can be generated by mutagenesis of a parent strain. Strategies and methods of mutagenesis, procedures for screening and isolation of mutated bacterial strains, composition of media used in producing the mutant strains of the invention are known in the art.

In the preferred embodiment, cultivation of *Photorhabdus khanii* DSM 3369, for the production of the compound of Formula (II) is carried out in a nutrient medium containing readily assimilable carbon soures, nitrogen sources, inorganic salts and other organic ingredients with one or more absorbents under proper aeration conditions and mixing in a sterile environment. Compositions of nutrient media used in producing antibiotics of the invention will be described in detail in the examples. (The term "nutrient medium" as used herein describes a mixture of synthetic or naturally occurring ingredients. In general, a nutrient medium comprises a carbon source, a nitrogen source, trace elements such as inorganic salts, and optionally vitamins or other growth factors.)

Figure 4:
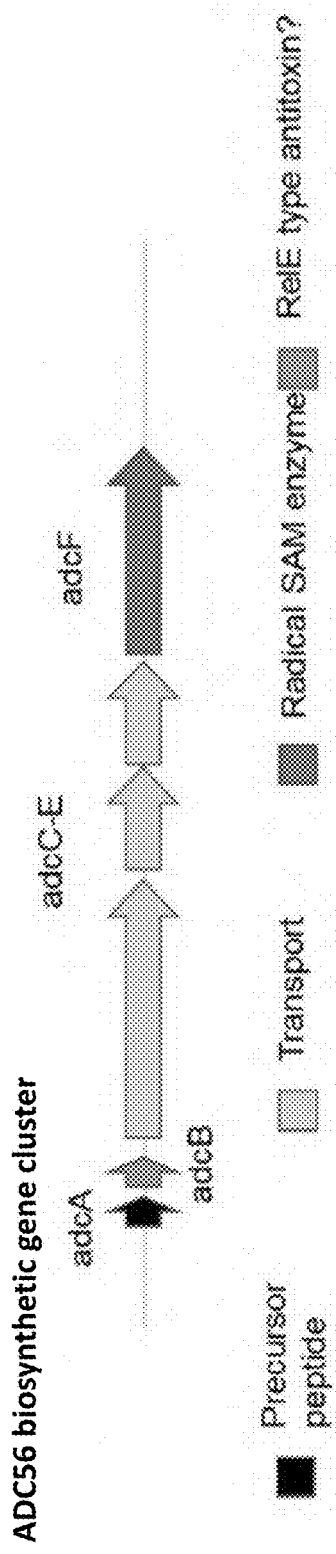
FIG. 4 graphically depicts the darobactin A biosynthetic gene cluster and alignments.

Analogs of the compounds described herein may be generated biosynthetically using straightforwardly obtained variations of the wild-type genome sequence encoding the present compounds. According to the genome sequence of *Photorhabdus khanii* DSM 3369 and as shown in FIG. 4, there is a match between the linearized amino-acid sequence of darobactin A, the compound of Formula (II) (WNWSKSF (SEQ ID NO: 1)), and part of a gene belonging to an operon typical for encoding RiPP (ribosomally synthesized and posttranslationally-modified peptides)-type antimicrobials. The operon contains a biosynthetic gene cluster that encodes, by nomenclature we here introduce, darA (coding for the precursor peptide of darobactin A, the compound of Formula (II)), darBCD (coding for a transporter, apparently for export of darobactin A), darE (a radical SAM enzyme required for formation of unactivated C—C bonds such as the trp-lys C—C bond of darobactin A). The 7aa sequence of darobactin A is shown within the precursor peptide. Sequence alignment demonstrates the presence of the dar operon in many *Photorhabdus*, with the core peptide being conserved.

*E. coli* mutants resistant to darobactin have been obtained, and they map to BamA, an essential component of the Bam complex that helps fold and insert proteins into the outer membrane.

The ribosomal encoding of darobactin A core peptide apparently means that all amino acids are in the L form. The ribosomal encoding enables production of analogs of darobactin A by nucleotide substitution in the darA gene coding for the precursor peptide. Such substitution may be achieved using any of various standard biochemical methods. Synthesis of the oligonucleotides with both specific and random substitutions of nucleotides of the coding region of darobactin A will produce a large array of fragments. These oligonucleotides will be ligated with upstream and downstream sequences coding for the precursor peptide, cloned into an expression vector, and transformed into cells carrying the dar operon with a disrupted precursor peptide gene. Darobactin A analogs are isolated from clones of this recombinant library and tested for activity. Analogs with increased potency against bacteria or improved pharmacological properties may be isolated and developed into drugs.

Where technically appropriate, embodiments may be combined and thus the disclosure extends to all permutations/combinations of the embodiments provided herein. The examples herein are for illustrative purposes only and they are not intended to limit the scope of the invention in any way.

EXAMPLES

Fermentation

*Photorhabdus khanii* DSM 3369 was inoculated into 10 ml Luria Bertani broth (LBB), and incubated at 28° C. with shaking (200 rpm) in 50 ml falcon tube. Ten milliliter overnight culture was inoculated into 1 L Tryptic Soy Broth (TSB) in 2 L Erlenmeyer flask, and incubated at 28° C. with shaking (200 rpm) for 8 to 10 days.

Isolation

Bacterial cells were removed by centrifugation (8,000×g, 10 min), and supernatant was recovered. Supernatant was mixed (4:1; v/v) with activated styrene-divinylbenzene resin (AMBERLITE XAD16N, SIGMA-ALDRICH), and followed by gentle shaking overnight under ambient temperature. Unbound material was removed by decanting and a compound, darobactin A (corresponding to Formula (II)), adsorbed on the resin, was washed with six times of resin volume of dd-water. darobactin A was eluted with four times resin volume of 50% methanol with 0.1% (v/v) formic acid by gentle shaking on rotary shaker for 30 min. The eluate was concentrated by rotary evaporator to remove organic solvent. The remaining aqueous eluate was acidified with 0.1% (v/v) of formic acid and then subjected to cation-exchange (SP Sepharose XL, GE Healthcare) chromatography in loose-resin bulk process. The activated cation-exchange resin was added to the acidified aqueous eluate and gently shaken for overnight at 4° C. Unbound material was decanted and resin was washed with 0.1% (v/v) formic acid dd-water. The antibiotic actives were eluted by step-gradients of 50 mM ammonium acetate pH 5, 50 mM ammonium acetate pH 7, and 50 mM ammonium acetate pH 8. The antibiotic active eluates were combined, freeze-dried, and then re-suspended in 0.1% (v/v) formic acid dd-water. The resuspension was subjected to second cation-exchange chromatography on four HiTrap SP XL cartridges in serial connected (5 mL per cartridge; total 20 mL bed volume) by elution with stepwise pH gradients. Unbound material was washed with 0.1% (v/v) formic acid dd-water, then eluted by step-gradients of 50 mM ammonium acetate pH 5, 50 mM ammonium acetate pH 7, and 50 mM ammonium acetate pH 8. The antibiotic active eluates were combined, freeze-dried, and then re-suspended in 0.1% (v/v) formic acid dd-water to subject to reverse-phase high performance chromatography (RP-HPLC) on C18 semi-preparative column (Agilent, C18, 5 µm; 250×10 mm, Restek), a linear gradient of water+0.1% (v/v) formic acid on solvent-A/acetonitrile+0.1% (v/v) formic acid on solvent-B starting from 2% B to 14% B in 14 min with a flow rate of 5 mL/min, UV detection from 210 to 400 nm monitoring at diode-array detector, yielding darobactin A at 12.25 min (purity: 95% UV).

Structure of Darobactin A darobactin A was isolated as an amorphous white powder after lyophilization.

The chemical tests on darobactin A indicated the presence of primary amine as it showed positive reaction with ninhydrin reagent. It also reacted positively to the ferric chloride test indicating the presence of phenol.

The High Resolution Electrospray Ionization Mass Spectrometry (HRESIMS) obtained on a THERMO SCIENTIFIC LTQ Orbitrap XL Hybrid Ion Trap-Orbitrap Mass Spectrometer by direct injection of darobactin A at a concentration of 1 µg/ml showed a $[M+2\ H]^{2+}$ peak at m/z 483.70874 and a $[M+H]^+$ peak at m/z 966.41046. The isotopic pattern indicated the absence of Cl or Br. The exact masses and the isotopic distribution were consistent with an elemental formula of $C_{47}H_{55}O_{12}N_{11}$.

One- and two-dimensional nuclear magnetic resonance (1D and 2D NMR) analyses of 5 mg of darobactin A solubilized in 500 µL of water+3% (v/v) deuterium oxide and 0.25% (v/v) formic acid deuterated on a Bruker 500 MHz indicated a peptide and revealed the presence of phenylalanine, two serines, lysine, two tryptophans and asparagine. The COSY, TOCSY, NOESY and HMBC spectra allowed the determination of the connection of the different amino acids by peptide bond and revealed an unusual lysine-to-tryptophan crosslink. This connection might result from a post-translational modification previously described by R. Schramma et al. 2015, involving a covalent linkage between two unactivated carbons within the side chains of lysine and tryptophan.

Acid hydrolysis of darobactin A, followed by derivatization with Marfey's reagent and LC-MS amino acid determination experiment and the analysis of the fragmentation pattern of the entire compound by tandem mass spectrometry (MS/MS) confirmed the peptide's sequence indicating a new natural product.

Antibacterial Spectrum

The minimum inhibitory concentrations (MIC) of darobactin A was determined by broth microdilution assay. The following test organisms were used for evaluating the spectrum of darobactin A: *Pseudomonas aeruginosa*, *Escherichia coli*, *Acinetobactor baumannii*, *Klebsiella pneumoniae*, *Staphylococcus aureus*, *Salmonella Typhimurium*, *Shigella sonnei*, *Enterobacter cloacae*, *Bacteroides fragilis*, *Lactobacillus reuteri*, and *Enterococcus faecalis*.

The test organisms were inoculated into 5 mL Muller Hinton II Broth (MHIIB) for aerobic condition or Brain Heart Infusion broth (BHI) for anaerobic condition, and grown until the cell density reach to $OD_{600}$=0.1-0.9. The cell suspension was diluted to $OD_{600}$=0.001, and 96 µL of bacterial culture were added to 4 µL darobactin A in 96 well plates (final concentrations 0.5 to 128 µg/mL). After incubation at 37° C. for 20 hours, growth of test organisms was determined visually (Table 1).

TABLE 1

MIC of darobactin A against test organisms

| Strain | darobactin A MIC (µg/mL) |
|---|---|
| Aerobic conditions | |
| Pseudomonas aeruginosa | 2 |
| Polymyxin resistant mutant (pmrB 523C > T) | 2 |
| Escherichia coli | 4 |
| E. coli + 10% serum | 2 |
| Polymyxin resistant mutant (AR350) | 2 |
| Acinetobacter baumannii | 8 |
| Klebsiella pneumoniae | 2 |
| Staphylococcus aureus | >128 |
| Anaerobic condition | |
| Pseudomonas aeruginosa | 1 |
| Escherichia coli | 2 |
| Salmonella Typhimurium | 2 |
| Shigella sonnei | 1 |
| Enterobacter cloacae | 32 |
| Bacteroides fragilis | >128 |
| Lactobacillus reuteri | >128 |
| Enterococcus faecalis | >128 |

MIC was determined by broth microdilution assay. The spontaneous polymyxin-resistant mutant of *P. aeruginosa* was isolated.

Cytotoxicity

HepG2 and FaDu cells were cultured in 20 mL Minimum Essential Medium (MEM)+10% fetal bovine serum (FBS) and 1% antibiotic-antimycotic solution in 75 cm² tissue culture flasks, and incubated at 37° C. with 5% $CO_2$ for 5 days (until cells reached 70% confluency) The growth medium was removed, and the cells were rinsed with 5 mL 1× phosphate buffered saline (PBS). After rinsing, the PBS was removed, and 2 mL 1×EDTA solution containing 0.25% trypsin was added. The cells were incubated for 2 minutes at 37° C. with 5% $CO_2$ to allow cells to detach from the flask. The trypsin was deactivated by added 6 mL culture medium to the flask, and the cells were detached by gentle pipetting in order to avoid clumping. The cells were counted and diluted to $2\times10^5$ cells/mL in MEM+10% FBS, and 100 µl of this suspension was added to clear, flat bottom, tissue culture treated 96 well plates. The plates were incubated overnight at 37° C. with 5% $CO_2$ to allow the cells to adhere to the plates.

In a separate clear, round bottom, non-tissue culture treated 96 well plate, 4 µl of darobactin A was mixed with 96 µl of culture medium. The supernatant was removed from each tissue culture plate, and the culture medium containing darobactin A was transferred from the round bottom plate to the tissue culture plates. The cells were incubated in the presence of darobactin A for 3 days at 37° C. with 5% $CO_2$, at which point 5 µl of 3 mM resazurin (Alamar Blue) was added. The plate was incubated for 3 hours at 37° C. with 5% $CO_2$. The viability of each cell line was evaluated by reading the fluorescence on a plate reader (554 nm/590 nm) (Table 2).

TABLE 2

Cytotoxicity of darobactin A against human cell lines

| Cell line | IC50 (µg/mL) |
|---|---|
| HepG2 | >128 |
| FaDu | >128 |

HepG2 and FaDu cells were treated with darobactin A, and 50% inhibitory concentration (IC < 50) of darobactin A was calculated by resazurin (Alamar blue/MABA) assay.

Killing Activity of Darobactin A

Figure 3:
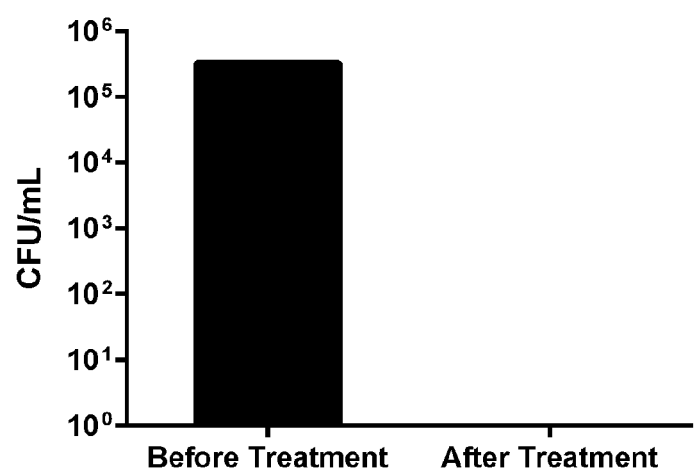
FIG. 3 is a graph showing the results of in vitro activity of the compound of Formula (II) against *E. Coli*. The compound of Formula (II) showed bactericidal activity. *E. coli* was grown to early exponential phase, and treated with 2×MIC of the compound of Formula (II) After 20 hours incubation, *E. coli* culture was plated for enumeration of live cells.

*E. coli* was inoculated into 5 mL Mueller Hinton II Broth (MHIIB), and grown to $OD_{600}$=0.1-0.9. The cell suspension was diluted to $OD_{600}$=0.001. 98 µL of *E. coli* culture was treated with 2 µL of darobactin A (16 µg/mL, corresponding to 2×MIC) in a 96-well plate, and incubated at 37° C. for 20 hours. The *E. coli* culture was plated onto antibiotic free Luria Broth agar, and colony forming units (CFU) were counted for enumeration of live cells (FIG. 3).

Antagonization Assay by Lipopolysaccharide (LPS)

darobactin A is a large compound of 966 Da molecular weight. The limit for penetration into Gram-negative bacteria is around 500 Da. It therefore seemed possible that darobactin A acted on the cell surface, similarly to polymyxin which targets lipopolysaccharide (LPS). In order to test this, activity of darobactin A was tested in the presence of LPS. *E. coli* was inoculated into 5 mL MHIIB, and grown until the cell density reach to $OD_{600}$=0.1-0.9. The cell suspension was diluted to $OD_{600}$=0.002 with 2×MHIIB. 40 µL of LPS solution (final concentration range from 0 to 800 µg/mL) and 2 µL of 2×MIC antibiotic solution (final concentration: polymyxin; 0.5 µg/mL, ampicillin; 16 µg/mL, darobactin A; 16 µg/mL) were mixed in a 96-well plate and fill up to 50 µL by sterile dl water. LPS and antibiotic solutions were mixed with 50 µL of *E. coli* cell suspensions, and incubated at 37° C. for 20 hours. The growth of *E. coli* was determined visually (Table 3).

TABLE 3

Antagonization of darobactin A antibacterial activity by LPS

| Antibiotic | LPS (µg/mL) | | | |
|---|---|---|---|---|
| | 0 | 3.13 | 6.25 | 800 |
| Polymyxin B | − | − | + | + |
| Ampicillin | − | − | − | − |
| darobactin A | − | − | − | − |

Figure 5A:
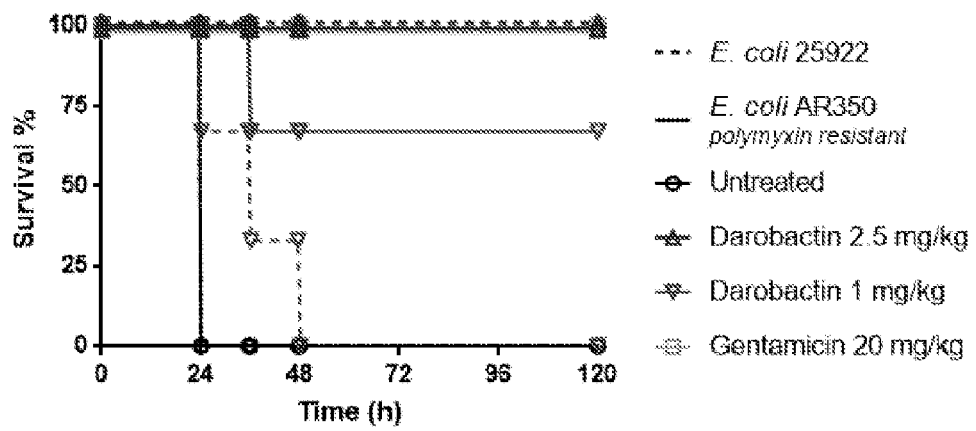
FIG. 5A is a graph showing the results of the in vivo efficacy of darobactin A in the *E. coli* septicemia model. The graph shows the survival rates of the mice with *E coli*. Septicemia. darobactin A was able to cure mice of *E. coli* septicemia at 2.5 mg/kg (ip), both ATCC 25922 and the polymyxin resistant clinical isolate AR350, n=3 per treatment group. The treatment was 1 h post infection. darobactin A at 1 mg/kg (ip) prolonged survival and significantly reduced CFU burden in blood at 5 h. Gentamicin was used as a positive control, given at 20 mg/kg.
Figure 5B:
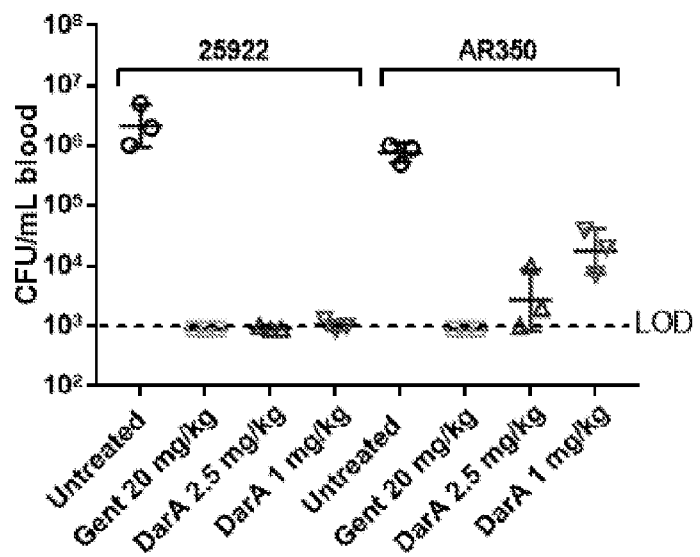
FIG. 5B is a graph showing the results of a colony-forming units per milliliter (CFU/mL) in the blood of the mice with *E coli*. Septicemia. darobactin A was able to cure mice of *E. coli* septicemia at 2.5 mg/kg (ip), both ATCC 25922 and the polymyxin resistant clinical isolate AR350, n=3 per treatment group. The treatment was 1 h post infection. darobactin A at 1 mg/kg (ip) prolonged survival and significantly reduced CFU burden in blood at 5 h. Gentamicin was used as a positive control, given at 20 mg/kg.
Figure 5C:
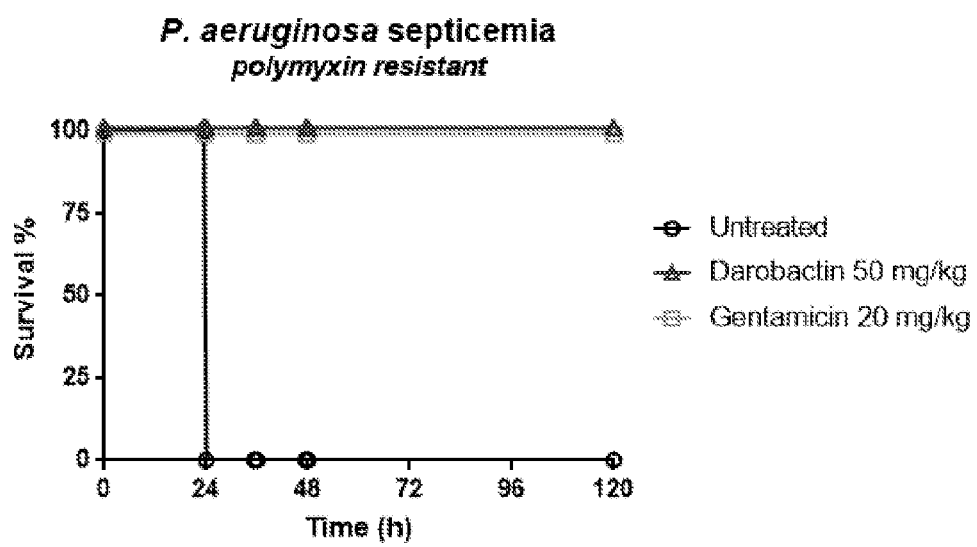
FIG. 5C is a graph showing the results of the in vivo efficacy of darobactin A in the *P. aeruginosa* septicemia model. darobactin A was tested at 50 mg/kg against *P. aeruginosa* P7-PA01 (lab isolate resistant to polymxyin) septicemia and was also able to completely cure the mice, n=3 per group. Gentamicin was used as a positive control, given at 20 mg/kg.
Figure 5D:
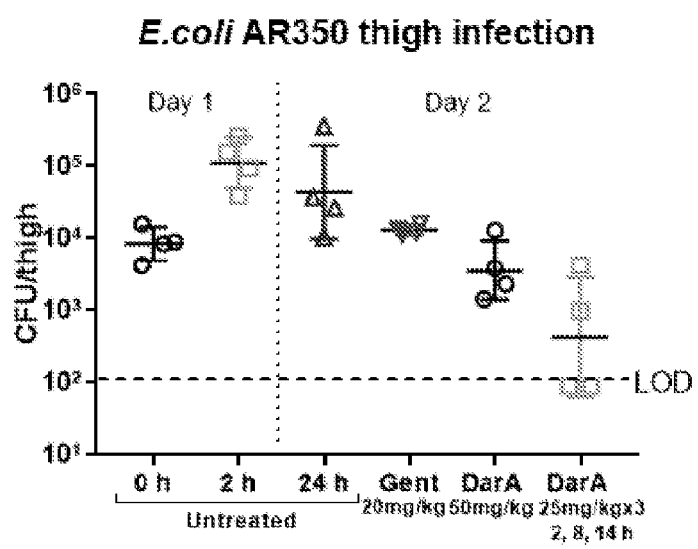
FIG. 5D is a graph showing the results of the in vivo efficacy of darobactin A in the *E. coli* neutropenic thigh infection model. In the thigh model, darobactin A 50 mg/kg (ip) at 2 h post infection had reduced CFU burden in the thigh by one log compared to untreated controls at 24 h, and 25 mg/kg (ip) given three times at 2, 8, and 14 h reduced the CFU burden by two logs, including to below the limit of detection in two mice, n=4 per group. Gentamicin was used as a positive control, given at 20 mg/kg.

LPS was incubated with 2 × MIC antibiotics, and growth effect on *E. coli* was monitored. Polymyxin and ampicillin were used as control.
+ : grown,
− : not grown Animal Efficacy Darobactin A has been tested in two animal efficacy models (FIG. 5). In the septicemia model, mice were injected with $10^6$ bacteria in 5% mucin (ip), an inoculum that caused 100% lethality in untreated groups within 24 h (FIGS. 5A, 5C). At 1 h post infection, in groups of three, mice were treated with Gentamicin 20 mg/kg as a positive control, or darobactin A at various dose levels. Survival was monitored over five days. darobactin A effectively treated the infection and gave 100% survival against *E. coli* at 2.5 mg/kg, both the commonly used ATCC 25922 strain and a clinical isolate resistant to polymyxin, AR350 (FIG. 5A). At 5 h blood was taken from tail snips to plate for CFU, which showed significant reduction in *E. coli* burden with darobactin A treatment (FIG. 5B) At 1 mg/kg, darobactin A still prolonged survival, but was no longer 100% curative (FIG. 5A). darobactin A was tested at 50 mg/kg against *P. aeruginosa* septicemia, using a lab strain resistant to polymyxin, and gave 100% survival (FIG. 5C). darobactin A was then tested for efficacy in the neutropenic mouse thigh model. Mice were given cyclophosphamide to induce neutropenia (day −3, day 0), then infected with $10^6$ CFU *E. coli* AR350 in their right thigh (day 1) and treatment initiated 2 h post infection. Untreated controls, four mice per group, were sacked at 0, 2, and 24 h to monitor infection progression.

darobactin A at 50 mg/kg single injection at 2 h (ip), was compared to darobactin A 25 mg/kg given three times (ip) at 2, 8, 14 h post infection, and Gentamicin 20 mg/kg single injection at 2 h (ip), four mice per treatment group. Mice were sacked at 24 h, thighs aseptically removed, homogenized, and plated on agar plates to enumerate CFU (FIG. 5D). darobactin A 50 mg/kg reduced the burden of infection one log compared to untreated controls, and 25 mg/kg given three times reduced the infection two logs, including to below the limit of detection in two mice.

Thus, darobactin A was able to cure mice of E. coli septicemia at 2.5 mg/kg (ip), both ATCC 25922 and the polymyxin resistant clinical isolate AR350, n=3 per treatment group, treatment was 1 h post infection. darobactin A at 1 mg/kg (ip) prolonged survival and significantly reduced CFU burden in blood at 5 h (A,B).

The terms and expressions employed herein are used as terms and expressions of description and not of limitation, and there is no intention, in the use of such terms and expressions, of excluding any equivalents of the features shown and described or portions thereof. In addition, having described certain embodiments of the invention, it will be apparent to those of ordinary skill in the art that other embodiments incorporating the concepts disclosed herein may be used without departing from the spirit and scope of the invention. Accordingly, the described embodiments are to be considered in all respects as only illustrative and not restrictive.

What is claimed is:

1. A compound of Formula (I):

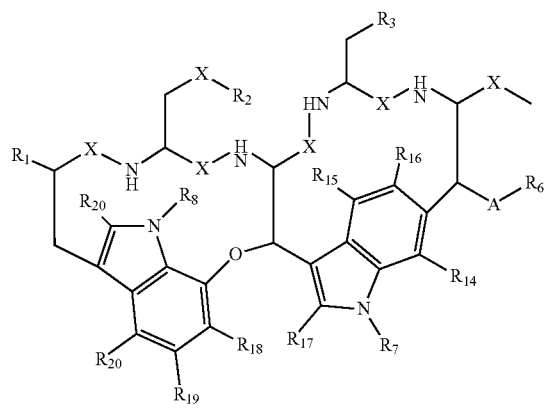

Formula (I)

and/or a pharmaceutically acceptable salt, stereoisomer, tautomer, or hydrate thereof, wherein:

$R_1$, $R_2$, $R_3$, $R_4$, $R_5$, and $R_6$ are each independently selected from the group consisting of hydrogen, alkyl, alkenyl, alkynyl, hydroxyl, hydroxyalkyl, halogen, —CN, —O-alkyl, —C(O)-alkyl, —C(O)O-alkyl, —C(O)OH, —C(O)NH$_2$, —C(O)NH-alkyl, —NH$_2$, —NO$_2$, —CF$_3$, —NH-alkyl, —N-(alkyl)$_2$, —NHC(O)-alkyl and aryl, wherein said alkyl, alkenyl, alkynyl and aryl are each optionally substituted;

$R_7$ and $R_8$ are each independently selected from the group consisting of hydrogen, straight or branched C1-C5 alkyl, straight or branched C2-C6 alkenyl, straight or branched C2-C6 alkynyl; wherein said alkyl, alkenyl and alkynyl are each optionally substituted;

$R_9$, $R_{10}$, $R_{11}$, $R_{12}$, $R_{13}$, $R_{14}$, $R_{15}$, $R_{16}$, $R_{17}$, $R_{18}$, $R_{19}$ and $R_{20}$ are each independently selected from the group consisting of hydrogen, alkyl, alkenyl, alkynyl, cycloalkyl, cycloalkenyl, heterocycloalkyl, heterocycloalkenyl, aryl, heteroaryl, haloalkyl, hydroxyl, hydroxyalkyl, halogen, —CN, —O-alkyl, —C(O)-alkyl, —C(O)O-alkyl, —C(O)OH, —C(O)N H$_2$, —C(O)NH-alkyl, —NH$_2$, —NO$_2$, —CF$_3$, —NH-alkyl, —NHC(O)-alkyl, wherein said alkyl, alkenyl, alkynyl, cycloalkyl cycloalkenyl, heterocycloalkyl, heterocycloalkenyl, aryl, heteroaryl, haloalkyl are each optionally substituted; A is a bond or —(CH$_2$)$_n$—, wherein n is an integer between 0 and 10; and X is —C(O)—, —CH$_2$—, —C(OH)—, —C(O)O-alkyl, —C((O)alkyl)-, with the provision that the compound of formula (I) is isolated in a substantially pure form from a microorganism; is encoded by a darA gene comprising at least one non-natural nucleotide substitution; and is neither naturally occurring nor the compound of formula (II):

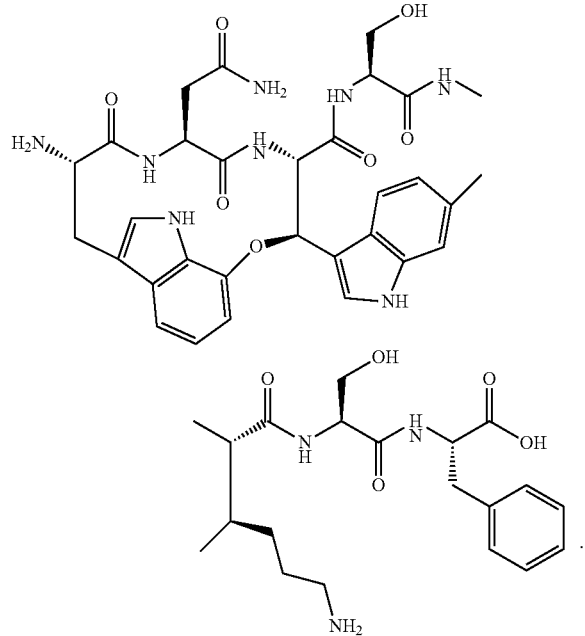

Formula (II)

2. A pharmaceutical composition for treating infections in an animal caused by Gram-negative bacteria, comprising a therapeutically effective amount of the compound according to claim 1 or a pharmaceutically acceptable salt thereof.

3. The pharmaceutical composition according to claim 2, further comprising at least one pharmaceutically acceptable carrier, excipient or diluent.

4. The pharmaceutical composition according to claim 2, in a form of topical administration, systemic administration, parenteral administration, subcutaneous administration, or transdermal administration, rectal administration, oral administration, intravaginal administration, intranasal administration, intrabronchial administration, intraocular administration, intra-aural administration, intravenous administration, intramuscular administration, or intraperitoneal administration.

5. The pharmaceutical composition according to claim 2, further comprising at least one additional therapeutic agent.

6. The pharmaceutical composition according to claim 2, obtained by culturing a microorganism having an ability to produce the compound in a nutrient medium.

7. The pharmaceutical composition according to claim 6, wherein the microorganism is *Photorhabdus khanii* DSM 3369.

* * * * *

SEQUENCE LISTING

<160> NUMBER OF SEQ ID NOS: 1

<210> SEQ ID NO 1
<211> LENGTH: 7
<212> TYPE: PRT
<213> ORGANISM: Photorhabdus sp.

<400> SEQUENCE: 1

Trp Asn Trp Ser Lys Ser Phe
1               5